US00PP11434P

United States Patent [19]

Pieters

[11] Patent Number: Plant 11,434

[45] Date of Patent: Jun. 27, 2000

[54] CHRYSANTHEMUM PLANT NAMED 'DARK OZENDA'

[76] Inventor: Dirk Pieters, Schierveldestraat 3A, Oosnieuwkerke, 8840 Staden, Belgium

[21] Appl. No.: 09/126,001

[22] Filed: Jul. 29, 1998

[51] Int. Cl.[7] ..... A01H 5/00

[52] U.S. Cl. ..... Plt./286

[58] Field of Search ..... Plt./286, 287, 293, Plt./298

[56] References Cited

U.S. PATENT DOCUMENTS

P.P. 10,419 5/1998 Pieters ..... Plt./287

OTHER PUBLICATIONS

UPOV–ROM, Feb. 1999, Plant Variety Database, GTI Jouve Retrieval Software, citation for 'Dark Ozenda'.

*Primary Examiner*—Howard J. Locker
*Attorney, Agent, or Firm*—Christie, Parker & Hale, LLP

[57] ABSTRACT

A new variety of chrysanthemum producing red-purple flowers.

1 Drawing Sheet

BACKGROUND OF THE INVENTION

The present invention is directed to a new and distinct variety of chrysanthemum botanically classified as *Dendranthema grandiflora*. The varietial denomination of the new chrysanthemum is 'Dark Ozenda'.

The new variety was discovered as a whole plant natural mutation of the variety 'Ozenda' (U.S. Plant Pat. No. 10,419) in Staden, Belgium. The new variety has been asexually reproduced by vegetative cuttings in Ventura County, Calif. and the distinguishing characteristics are retained through successive generations of asexual reproduction.

SUMMARY OF THE INVENTION

'Dark Ozenda' is a chrysanthemum plant variety that produces red-purple decorative-type flowers.

COMPARISON WITH PARENT

The new variety differs from its parent in having red-purple flowers.

BRIEF DECRIPTION OF ILLUSTRATION

The accompanying photograph shows a typical specimen of the new variety with colors being as nearly true as possible with illustrations of this type.

DESCRIPTION OF THE PLANT

The following description of the new variety is of specimens grown in a greenhouse in Ventura County, Calif. in the month of April. 'Dark Ozenda' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once about ten days after planting. It has been observed that the shelf life of 'Dark Ozenda' is about 26 days with the response time of about 7 weeks. No growth regulator is used with the plants described. Desirable growing conditions include average night temperatures of about 62°–64° F. and day temperatures of about 70°–75° F.

Plant:

*Habit*.—Herbaceous mounding perennial. Free branching.

*Height*.—About 28 cm.

*Number of breaks from pinch*.—About 4 to 5.

*Length of lateral branches*.—About 22 cm.

*Stem color*.—Near 138B.

Foliage:

*Leaf arrangement*.—Alternate.

*Number of leaves per lateral branch*.—10 fully expanded leaves.

*Leaf size*.—Length: About 6 cm. Width: About 3.3 cm.

*Leaf shape*.—Ovate.

*Attachment*.—Petioled.

*Leaf apex*.—Acute.

*Base*.—Tapered.

*Margin*.—Palmately lobed, infrequent serrations.

*Aspect*.—Slightly undulate.

*Surface*.—Top: Lightly pubescent. Bottom: Lightly pubescent.

*Venation*.—Mid vein prominent on underside. Mid Vein Color: Underside: Near 146C. Upperside: Near 137D.

*Petiole*.—Length: About 1.6 cm. Color: Near 137D.

*Mature leaf color*.—Top: Near 137A. Bottom: Near 137D.

*Young leaf color*.—Top: Near 137B. Bottom: Near 138B.

Flower:

*Inflorescence form*.—Cyme.

*Flower form*.—Decorative-type inflorescence with slight open center.

*Number of blooms per branch*.—About 11.

*Diameter of fully expanded bloom*.—About 3.8 cm.

*Depth of fully expanded bloom*.—About 1.5 cm.

*Diameter of disc*.—About 1.3 cm.

*Sepal number*.—About 25. Color: Near 137B. Length: About 0.9 cm.

*Peduncle*.—Length: Longest peduncles occur on the lowermost part of the inflorescence; these average about 5.5 cm; terminal peduncle is shortest, averaging about 2.8 cm. Aspect: Weak, slightly undulating. Surface: Pubescent. Color: Near 138B.

*Flower bud* (*when just showing color*).—Color: Near 63B. Diameter: About 0.9 cm. Height: About 0.7 cm. Shape: Flattened spherical.

*Ray florets*.—Number per flower: About 120. Texture: Matte. Shape: Ovate. Apex: 3 obtuse lobes. Base: Truncate. Margin: Entire. Aspect: Slightly involute. Length: About 1.5 cm. Width: About 0.8 cm.

*Disc florets*.—Number per flower: About 10. Texture: Shiny. Shape: Cylindrical, fluted apex. Length: About 0.5 cm. Width: About 0.12 cm.

*Fragrance*.—Moderate.

Flower color:

*General flower coloration*.—Red-Purple.

*Ray florets, top side*.—Immature: Near 63B. Mature: Near 63A. Fading: Near 64C.

*Ray floret, under side*.—Immature: Near 64C. Mature: Near 64B. Fading: Near 64D.

*Disc florets*.—Immature: Near 2B. Mature: Near 13B. Fading: Near 4B.

*Changes as the flower ages*.—Color fades slightly.

Reproductive organs:

*Ray florets*.—Pistillate. Stigma shape: 2 branched. Stigma color: Near 12A. Style length: About 0.4 cm. Style color: Near 4D.

*Disc florets*.—Stigma shape: Linear. Stigma color: Near 2C. Style Length: About 0.3 cm. Style color: Near 2D. Stamen number: About 5. Anther length: About 0.2 cm. Pollen color: Near 15B. Pollen quantity: Moderate.

What is claimed is:

1. A new and distinct chrysanthemum plant of the variety substantially as herein shown and described.

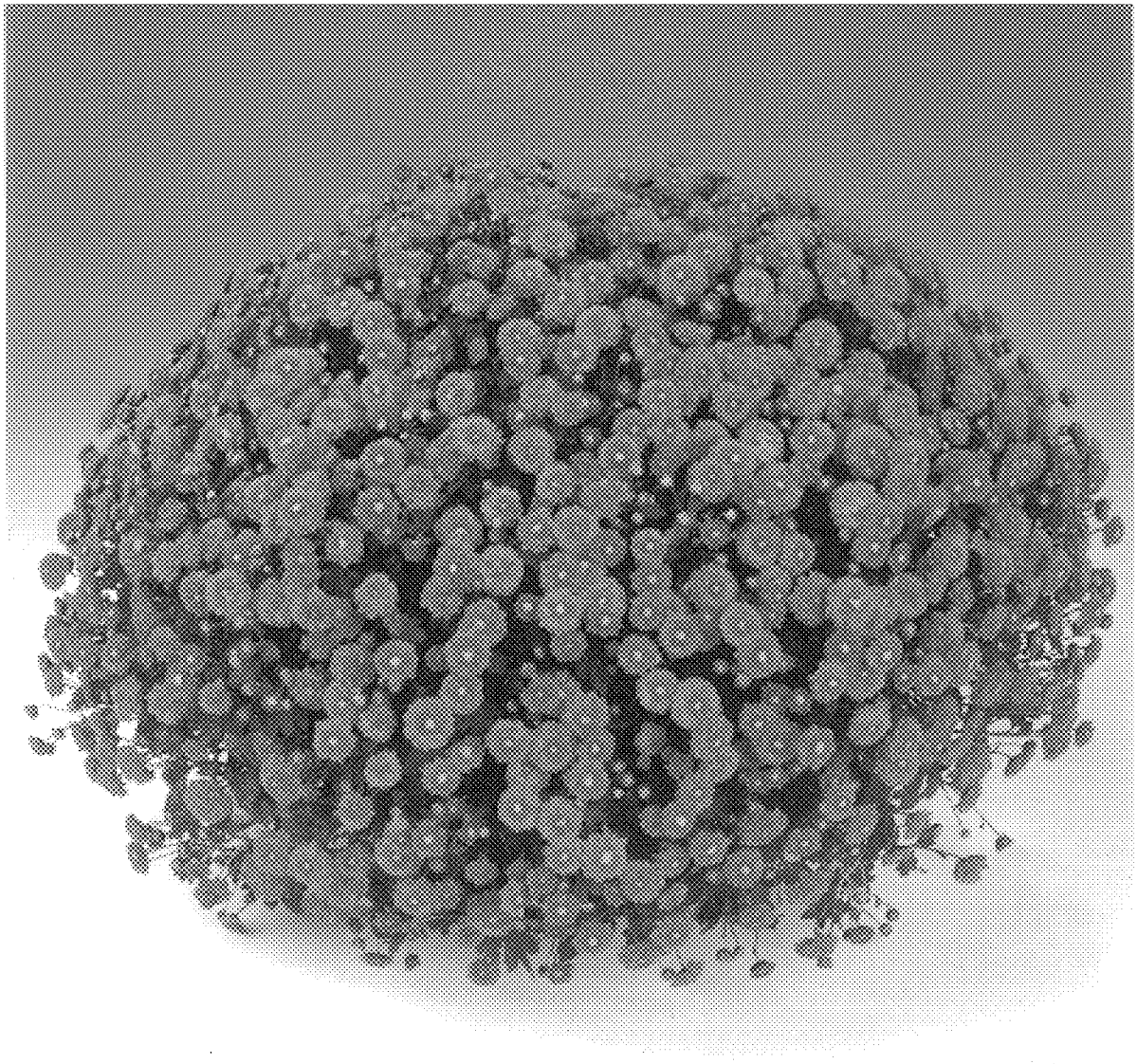

* * * * *